(12) United States Patent
Klapper

(10) Patent No.: US 9,649,346 B2
(45) Date of Patent: May 16, 2017

(54) PROBIOTIC STICK FORMULATION FOR SKIN MAINTENANCE AND METHODS OF USE

(71) Applicant: BIOS LLC, Long Beach, NY (US)

(72) Inventor: Andrew M. Klapper, Brooklyn, NY (US)

(*) Notice: Subject to any disclaimer, the term of this patent is extended or adjusted under 35 U.S.C. 154(b) by 211 days.

(21) Appl. No.: 14/355,782

(22) PCT Filed: Nov. 1, 2012

(86) PCT No.: PCT/US2012/063067
§ 371 (c)(1),
(2) Date: May 1, 2014

(87) PCT Pub. No.: WO2013/067185
PCT Pub. Date: May 10, 2013

(65) Prior Publication Data
US 2014/0301994 A1    Oct. 9, 2014

Related U.S. Application Data

(60) Provisional application No. 61/555,885, filed on Nov. 4, 2011, provisional application No. 61/554,709, filed on Nov. 2, 2011.

(51) Int. Cl.
| | | |
|---|---|---|
| A61K 38/44 | (2006.01) | |
| A61K 35/741 | (2015.01) | |
| A61Q 19/00 | (2006.01) | |
| A61Q 19/08 | (2006.01) | |
| A61K 8/99 | (2017.01) | |
| A61K 8/02 | (2006.01) | |
| A61K 35/747 | (2015.01) | |
| A61K 45/06 | (2006.01) | |

(52) U.S. Cl.
CPC .......... *A61K 35/741* (2013.01); *A61K 8/0229* (2013.01); *A61K 8/99* (2013.01); *A61K 35/747* (2013.01); *A61K 45/06* (2013.01); *A61Q 19/00* (2013.01); *A61Q 19/08* (2013.01); *A61K 2800/31* (2013.01)

(58) Field of Classification Search
None
See application file for complete search history.

(56) References Cited

U.S. PATENT DOCUMENTS

| | | | | |
|---|---|---|---|---|
| 4,518,696 A | * | 5/1985 | Gehrman | C12N 1/04 424/93.45 |
| 4,609,674 A | * | 9/1986 | Gupte | A61K 8/375 514/547 |
| 2004/0166074 A1 | * | 8/2004 | Darkwa | A61K 8/19 424/70.1 |
| 2005/0255070 A1 | * | 11/2005 | Albano | A61K 8/986 424/70.14 |
| 2009/0060962 A1 | | 3/2009 | Castiel et al. | |
| 2010/0260695 A1 | | 10/2010 | Burke-Colvin et al. | |
| 2011/0014248 A1 | | 1/2011 | Castiel et al. | |
| 2011/0064832 A1 | | 3/2011 | Burke-Colvin et al. | |
| 2011/0223219 A1 | | 9/2011 | Dao et al. | |

FOREIGN PATENT DOCUMENTS

| | | | |
|---|---|---|---|
| EP | 2477637 A1 | * | 7/2012 |
| KR | 20000039570 A | | 7/2000 |
| KR | 20080092090 A | | 10/2008 |

OTHER PUBLICATIONS

Morgan et al. J. Microbiol. Methods (2006) 66: 183-193.*
International Search Report of PCT/US2012/063067 dated Mar. 28, 2013.
International Preliminary Report on Patentability of PCT/US2012/063067 dated May 6, 2014.
Written Opinion of PCT/US2012/063067 dated Mar. 28, 2013.

\* cited by examiner

*Primary Examiner* — Susan Hanley
(74) *Attorney, Agent, or Firm* — Bryan D. Zerhusen; Locke Lord LLP

(57) ABSTRACT

The invention relates to an anhydrous mixture of biologically active probiotic bacteria for topical administration and methods of making thereof. The mixture of the invention is used for hydrating the skin, reducing and preventing fine lines and wrinkles, treating acne and decreasing skin inflammation.

29 Claims, 8 Drawing Sheets

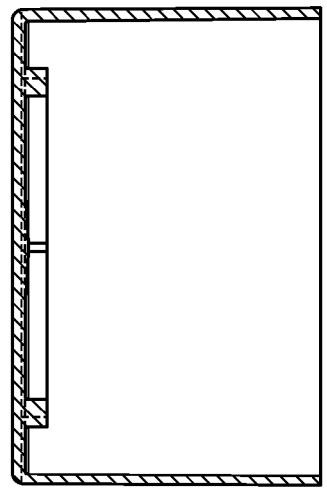
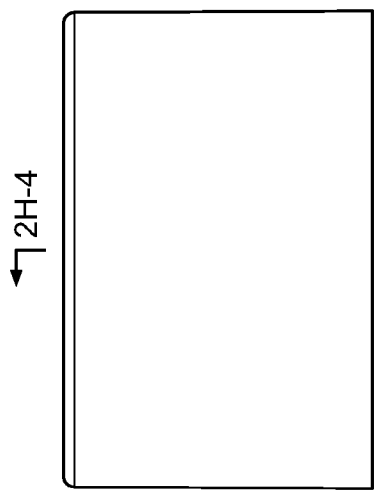
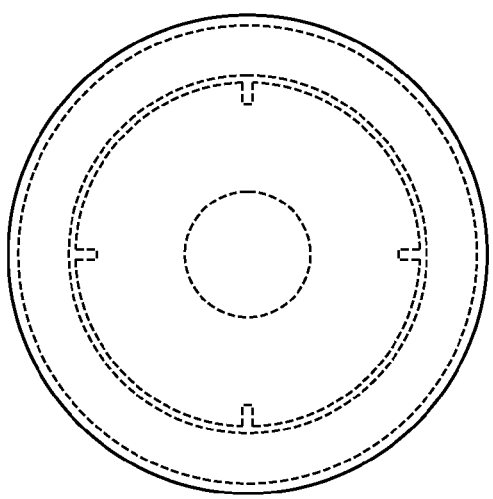
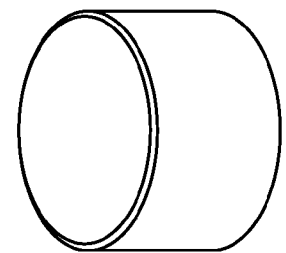

PROBIOTIC STICK FORMULATION FOR SKIN MAINTENANCE AND METHODS OF USE

CROSS REFERENCE TO RELATED APPLICATIONS

This application is the U.S. national phase, pursuant to 35 U.S.C. §371, of PCT international application Ser. No. PCT/US2012/063067, filed Nov. 1, 2012, designating the United States and published in English on May 10, 2013 as publication WO2013/067185 A1. PCT/US2012/063067 claims priority to U.S. Application No. 61/554,709, filed Nov. 2, 2011 and U.S. Application No. 61/555,885, filed Nov. 4, 2011. The entire contents of the aforementioned patent applications are incorporated herein by reference.

BACKGROUND OF THE INVENTION

Hydration of the horny layer of the epidermis is essential for keeping the skin smooth and soft, with no opacity or tendency for desquamation. Moreover, the maintenance of a correct skin hydration makes it possible to prevent and/or combat some of the effects of skin aging, in particular fine lines and wrinkles.

The term skin hydration refers to the water present in the horny layer of the epidermis. The horny layer consists of broad, flat cells (the corneocytes) immersed in a lipid matrix, which gives rise to an elastic cushion. On average, the horny layer consists of about 10 layers of cells about 1 micrometer thick, whose size depends on age, sex and various factors, both internal and environmental. To maintain its proper condition, the horny layer must contain water at a level that is at least 10% of its own weight. This water content is determined by the interaction of several factors: the influx of water from the deep layers of the skin, evaporation at the body surface, and the ability of the horny layer to retain water.

Lactic acid bacteria *Streptococcus thermophilus* has been proven to increase ceramide production in the skin when topically applied. Ceramides are the major lipid constituent of lamellar sheets present in the intercellular spaces of the stratum corneum. These lamellar sheets are thought to provide the barrier property of the epidermis. It is generally accepted that the intercellular lipid domain is composed of approximately equimolar concentrations of free fatty acids, cholesterol, and ceramides. Ceramides are a structurally heterogeneous and complex group of sphingolipids containing derivatives of sphingosine bases in amide linkage with a variety of fatty acids. Differences in chain length, type and extent of hydroxylation, saturation etc. are responsible for the heterogeneity of the epidermal sphingolipids.

It is well known that ceramides play an essential role in structuring and maintaining the water permeability barrier function of the skin. In conjunction with the other stratum corneum lipids, ceramides form ordered structures. At physiological temperatures, the lipid chains are mostly in a solid crystalline or gel state, which exhibit low lateral diffusional properties and are less permeable than the state of liquid crystalline membranes, which are present at higher temperatures.

With aging the ability of the skin to function as a barrier is decreased and there is a decrease in total ceramide content. Ceramide supplementation improves barrier function and improves fine lines and wrinkles.

Ceramide sphingolipids most notably phytosphingosine provide anti-microbial activities and direct anti-inflammatory activity. Sphingolipids have been noted to be low in acne, and the seasonal loss of ceramides have been noted to be a driving force behind much higher dermatological visits for acne during winter months.

Acne is a disorder of the pilosebaceous unit, which is made up of a hair follicle, sebaceous gland, and a hair. People with acne have more *Propionibacterium acnes* in their follicles than people without acne. The presence of bacteria attracts white blood cells to the follicle. These white blood cells produce an enzyme that damages the wall of the follicle, allowing the contents of the follicle to enter the dermis. This process causes an inflammatory response seen as papules (red bumps), pustules, and nodules. The bacteria also cause the formation of free fatty acids, which are irritants, increasing the inflammatory process in the follicle. *Streptococcus thermophilus* controls the overgrowth of Proprionis Acnes and decreases the sequella of acne *vulgaris*.

SUMMARY OF THE INVENTION

As described below, the present invention features a mixture comprising biologically active probiotic bacteria for topical administration. In one embodiment, the mixture is packaged as a push-up tube. The invention also provides for a method of preparing the mixture. The mixture provides for maintenance of probiotic bacteria in a non-proliferative state. The method also provides for methods of colonizing the skin with biologically active probiotic bacteria. Further, the invention provides for methods of using the composition for hydrating the skin, decreasing and/or preventing fine lines and wrinkles, limiting and reducing skin inflammation, decreasing/treating acne and decreasing the occurrence of future outbreaks of acne.

The present invention offers numerous advantages including, a mixture comprising all natural ingredients. When the mixture is presented in the form of a push-up stick, it can be easily applied.

The invention provides for a composition comprising an anhydrous mixture comprising a probiotic bacteria for topical administration to the skin.

In one embodiment, the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius*.

In another embodiment, the mixture comprises at least one of: propylene glycol, glycerin, stearyl alcohol, sodium stearate, kaolin, *Chamomilla recutita* flower extract, myristyl alcohol, silica, astaxanthin and inulin.

In another embodiment, the concentration of propylene glycol is about 30% to about 68%.

In another embodiment, the concentration of astaxanthin is about 0.01% to about 1%.

In another embodiment, the concentration of kaolin is about 1% to about 10%.

In another embodiment, the bacteria is provided as a milk ferment lysate.

In another embodiment, the concentration of the bacteria is about 1% to about 5%.

In another embodiment, the concentration of inulin is about 1% to about 5%.

In another embodiment, the concentration of stearyl alcohol is about 0.01% to about 20%.

In another embodiment, the concentration of sodium stearate is about 0.01 to about 10%

In another embodiment, the concentration on glycerin is about 0.01% to about-10%

In another embodiment, the concentration of *Chamomilla recutita* flower extract is about 0.01% to about 3%

In another embodiment, the concentration of myrsistyl alcohol is about 0.01% to about 5%.

In another embodiment, the concentration of silica is on the order of about 1% to about 10%.

In another embodiment, the composition comprises 65.96% propylene glycol, 2.64% glycerin, 11.37% stearyl alcohol, 1.11% myristyl alcohol, 7.07% sodium stearate, 1.33% chamomile extract, 1.11% silica, 3.88% kaolin, 2.77% inulin, 2.77% *Streptocossus thermophilus* 250 B and 0.01% astaxanthin.

In another embodiment, the bacteria are in a non-proliferative state prior to application to the skin.

In another embodiment, the mixture is packaged in a push-up tube or a pushscrew tube.

In one embodiment, the mixture is package in a push-up tube or a pushscrew tube is a solid form.

In another embodiment, the bacteria are freeze-dried.

In another embodiment, the mixture further comprises at least one of benzoyl peroxide, salicylic acid and sulfur.

In another embodiment, the composition hydrates the skin, decreases and/or prevents fine lines and wrinkles, limits and reduces skin inflammation, prevents future outbreaks of acne, and/or decreases acne that is already present on the skin The invention also provides for a stick comprising the composition of the invention.

In one embodiment, the stick comprises the composition of the invention in a solid form.

The invention also provides for a method of maintaining probiotic bacteria in a non-proliferative state comprising combining the bacteria with at least one of: propylene glycol, stearyl alcohol, sodium stearate, kaolin, glycerin, *Chamomilla recutita* flower extract, myrsistyl alcohol, silica, astaxanthin and inulin, to form an anhydrous solution.

The invention also provides for a method of colonizing the skin with probiotic bacteria comprising topically administering to the skin the composition of the invention to the skin.

The invention also provides for a method of decreasing acne/treating acne comprising topically administering to the skin the composition of the invention.

The invention also provides for a method of decreasing and/or preventing fine lines and wrinkles comprising topically administering to the skin the composition of the invention.

The invention also provides for a method of maintaining the hydration of the skin comprising topically administering to the skin the composition of the invention.

The invention also provides for a method of reducing skin inflammation comprising topically administering to the skin the composition of the invention.

In certain embodiments, the methods also require a step of identifying an individual in need of treatment. This identification can be performed by the individual and/or by a healthcare professional. In another embodiment, the results of the method are reported to a healthcare professional.

The invention also provides for a method of making an anhydrous mixture comprising probiotic bacteria for topical administration to the skin comprising combining the probiotic bacteria with at least one of propylene glycol, stearyl alcohol, sodium stearate, kaolin, glycerin, *Chamomilla recutita* flower extract, myrsistyl alcohol, silica, astaxanthin and inulin.

In one embodiment, the method further comprises a step of heating the propylene glycol to 75° C.

In another embodiment, each of the components of the mixture are added to a solution of propylene glycol.

In another embodiment, the method further comprising a step of heating the mixture to 50° C. prior to the addition of kaolin, and bacteria.

In another embodiment, the method comprises a step of freeze-drying the bacteria.

In another embodiment, the method comprises a step of solidifying the mixture.

The invention also provides for a composition comprising an anhydrous mixture comprising a probiotic bacteria for topical administration to the skin; wherein the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius;* further comprising at least one of: propylene glycol, glycerin, stearyl alcohol, sodium stearate, kaolin, *Chamomilla recutita* flower extract, myristyl alcohol, silica, astaxanthin and inulin; wherein the concentration of propylene glycol is about 30% to about 68%; and/or wherein the concentration of astaxanthin is about 0.01% to about 1%; and/or wherein the concentration of kaolin is preferably about 1% to about 10%; and/or wherein the concentration of the bacteria is preferably about 1% to about 5%; and/or wherein the concentration of inulin is about 1% to about 5%; and/or wherein the concentration of stearyl alcohol is about 0.01% to about 20%; and/or wherein the concentration of sodium stearate is about 0.01-about 10%; and/or wherein the concentration on glycerin is about 0.01% to about-10%; and/or wherein the concentration of *Chamomilla recutita* flower extract is about 0.01% to about 3%; and/or wherein the concentration of myrsistyl alcohol is about 0.01% to about 5%; and/or wherein the concentration of silica is about 1% to about 10%; optionally wherein the bacteria is provided as a milk ferment lysate; optionally further comprising at least one of benzoyl peroxide, preferably 2.5%, salicylic acid and sulfur; optionally wherein the bacteria are in a non-proliferative state prior to application to the skin; optionally wherein the mixture is packaged in a push-up tube; optionally wherein the mixture is packaged in a push-up tube as a solid; and optionally wherein the bacteria are freeze-dried.

The invention also provides for a stick comprising a composition comprising an anhydrous mixture comprising a probiotic bacteria for topical administration to the skin; wherein the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius;* further comprising at least one of: propylene glycol, glycerin, stearyl alcohol, sodium stearate, kaolin, *Chamomilla recutita* flower extract, myristyl alcohol, silica, astaxanthin and inulin; wherein the concentration of propylene glycol is about 30% to about 68%; and/or wherein the concentration of astaxanthin is about 0.01% to about 1%; and/or wherein the concentration of kaolin is preferably about 1% to about 10%; and/or wherein the concentration of the bacteria is preferably about 1% to about 5%; and/or wherein the concentration of inulin is about 1% to about 5%; and/or wherein the concentration of stearyl alcohol is about 0.01% to about 20%; and/or wherein the concentration of sodium stearate is about 0.01-about 10%; and/or wherein the concentration on glycerin is about 0.01% to about-10%; and/or wherein the concentration of *Chamomilla recutita* flower extract is about 0.01% to about 3%; and/or wherein the concentration of myrsistyl alcohol is about 0.01% to about 5%; and/or wherein the concentration of silica is about 1% to about 10%; optionally wherein the bacteria is provided as a milk ferment lysate; optionally further comprising at least one of benzoyl peroxide, preferably 2.5%, salicylic acid and sulfur; optionally wherein the bacteria are in a non-proliferative state prior to application to the skin; and optionally wherein the bacteria are freeze-dried.

The invention also provides for a method of making an anhydrous mixture comprising probiotic bacteria for topical administration to the skin comprising combining the probiotic bacteria with at least one of propylene glycol, stearyl alcohol, sodium stearate, kaolin, glycerin, *Chamomilla recutita* flower extract, myrsistyl alcohol, silica, astaxanthin and inulin; optionally comprising a step of heating the propylene glycol to 75° C.; optionally wherein each of the components of the mixture are added to a solution of propylene glycol; and optionally comprising a step of heating the mixture to 50° C. prior to the addition of kaolin, and bacteria.

DEFINITIONS

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not changed by the presence of more than that which is recited, but excludes prior art embodiments.

As used herein, "anhydrous" means containing no water.

As used herein, "probiotic bacteria" means live bacteria that are beneficial to the host organism. Probiotics are commonly consumed as part of fermented foods with specially added active live cultures; such as in yogurt, soy yogurt, or as dietary supplements. Probiotic bacteria useful according to the invention include but are not limited to *Streptococcus thermophilus, Streptococcus salivarus* subspecies *thermophilus* type 1131, *Bifidobacterium longum, Lactobacillus paracasei* and *Streptococcus salivarius.*

As used herein, "milk ferment lysate" means culture medium for bacteria.

As used herein, "non-proliferative" means do not increase in number. As used herein, a non-proliferative pro-biotic bacteria does not increase in number. As used herein, a non-proliferative bacteria increases in number by less than 10%, for example, 9%, 8%, 7%, 6%, 5%, 4%, 3%, 2% or 1%. Bacterial proliferation can be determined by methods well known in the art, for example, colorimetric assays, for example, as available from Invitrogen, wherein bacteria are detected using a dye, or by assays that measure new DNA synthesis As used herein, "push-up tube" or "push-up stick" means a cylindrical shaped container, preferably made of plastic, in which a solid form of the mixture of the invention is contained. For application, the solid mixture is moved upwards, preferably above the top edge of the container, either by pushing the solid from the bottom or by turning a disk located at the bottom of the tube. In one embodiment, the push-up tube is a screwpush tube. A push-up tube comprising a stick according to the invention is depicted in FIG. 1.

As used herein, "decreases" means reduces by at least 10%, 25%, 50%, 75%, or 100%. A decrease as it refers to fine lines wrinkles or acne is determined by visual examination. A decrease in fine lines and/or wrinkles refers to a decrease in the number or the intensity. A decrease in the level of acne refers to a decrease in redness and/or a decrease in the area over which the acne occurs. A decrease in the level of acne is determined by visual examination.

As used herein "prevents" decreases 100%. For example, prevents the occurrence of future outbreaks of acne means there is no occurrence of future outbreaks of acne while the mixture is being applied. Prevents, as it refers to fine lines and wrinkles means fine lines and wrinkles are not detected by visual examination.

As used herein, "stick" means a solid form of the mixture of the invention (see, for example, FIG. 1).

As used herein, "colonize" means become establish and divide.

BRIEF DESCRIPTION OF THE DRAWINGS

FIG. 2C-1 to FIG. 2C-3; FIG. 2D-1 to FIG. 2D-4; FIG. 2E-1 to 2E-5; FIG. 2F-1 to 2F-5; FIG. 2G-1 to 2G-6; and FIG. 2H-1 to 2H-4) presents detailed schematics of the screwpush tube of the invention.

DETAILED DESCRIPTION OF THE INVENTION

Figure 1:
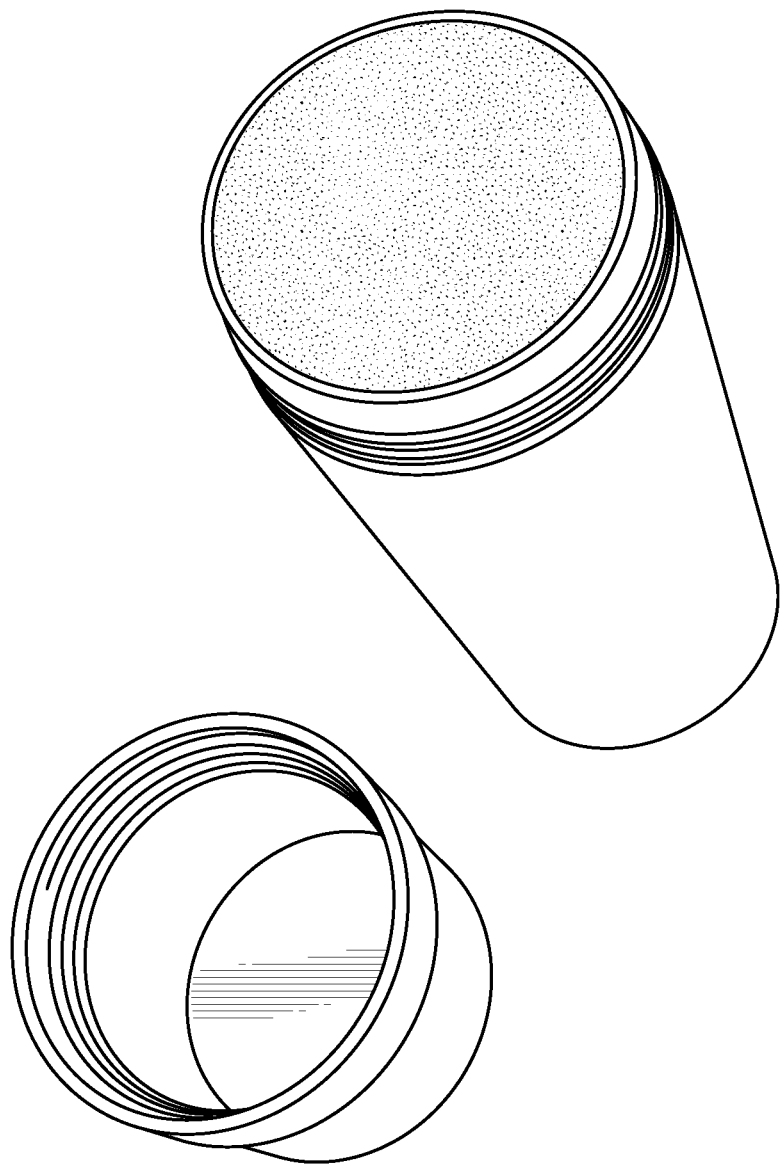
FIG. 1 presents the composition of the invention packaged in a push-up tube. The composition is in the form of a solid. The solid has an white color. The freeze dried bacteria are visible as black specs on the surface of the solid.
Figures 2, 2A, 3, 4, 5:
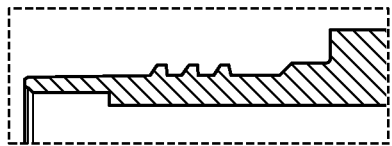
Figures 2, 2A, 3, 4:
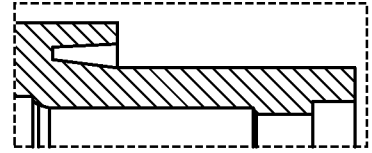
Figures 2, 2A:
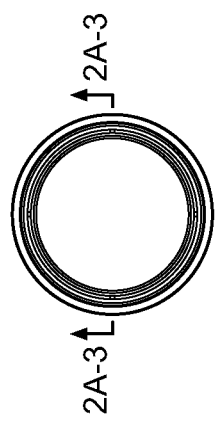
FIG. 2 (which includes FIG. 2A-1 to FIG. 2A-5.
Figures 2, 2A, 3:
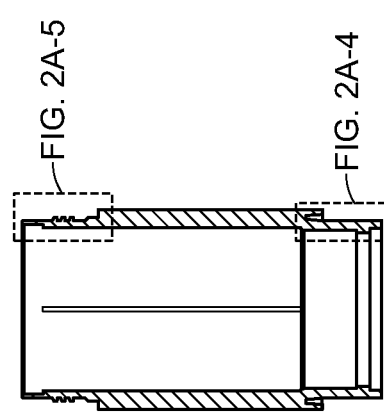
Figures 1, 2A:
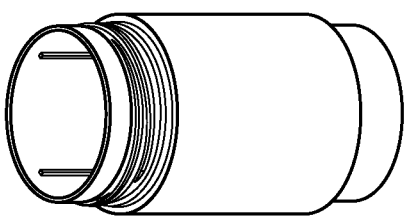
Figures 2, 2C, 3:
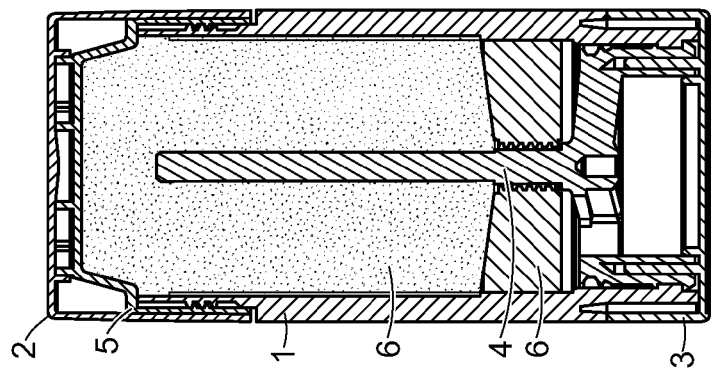
Figures 1, 2C:
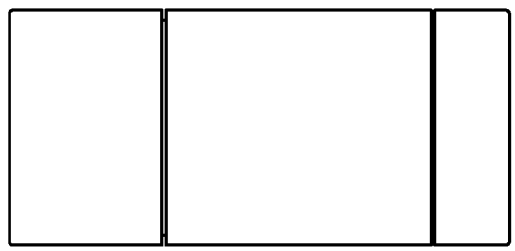
Figures 2, 2C:
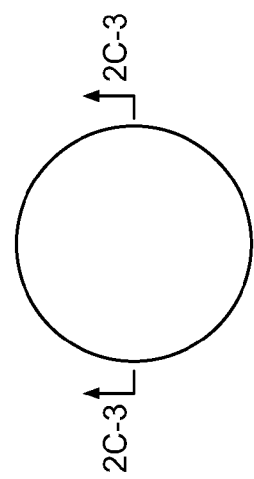
Figure 2B:
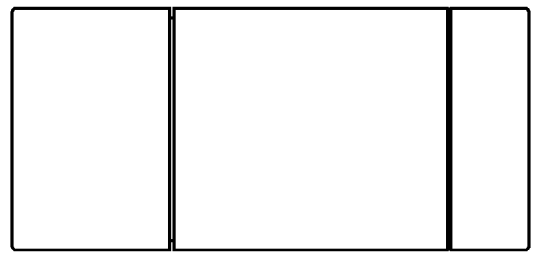
FIG. 2B.
Figures 2, 2D, 3, 4:
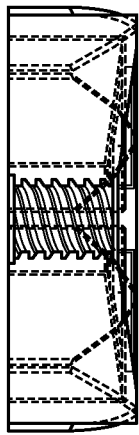
Figures 2, 2D:
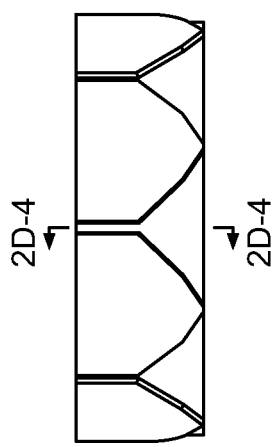
Figures 2, 2D, 3:
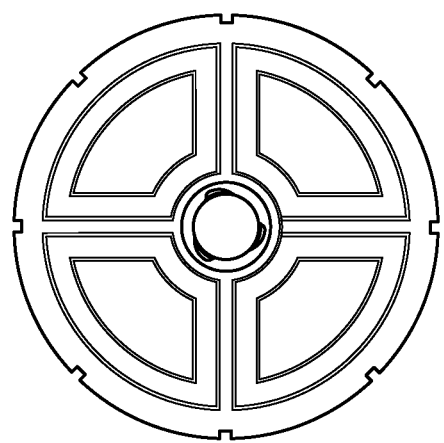
Figures 1, 2D:
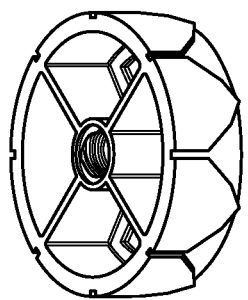
Figures 2, 2E, 3, 4:
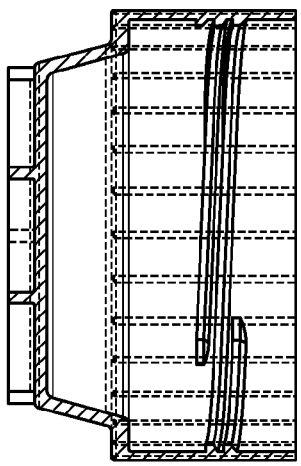
Figures 2, 2E, 3, 4, 5:
Figures 2, 2E:
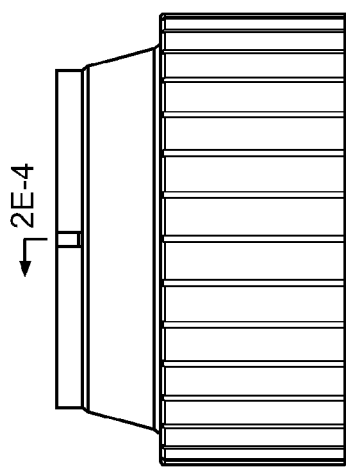
Figures 2, 2E, 3:
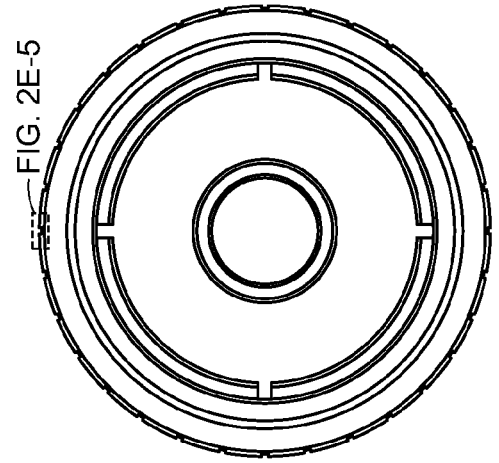
Figures 1, 2E:
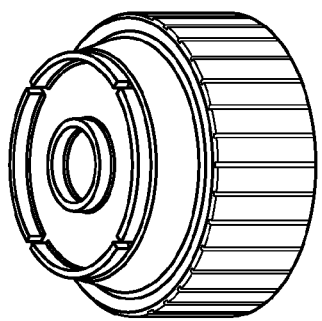
Figures 2, 2F, 3, 4, 5:
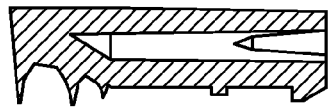
Figures 2, 2F, 3, 4:
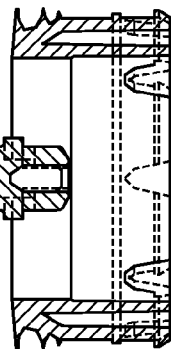
Figures 2, 2F:
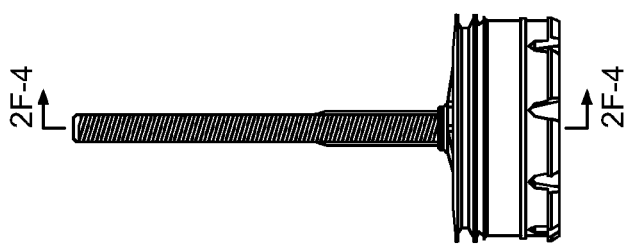
Figures 2, 2F, 3:
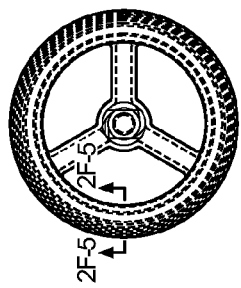
Figures 1, 2F:
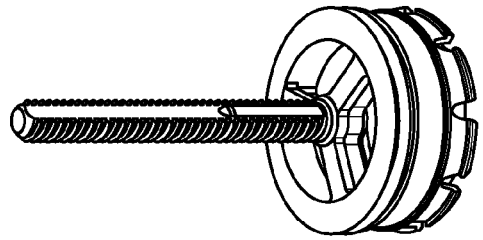
Figures 2, 2G, 3, 4:
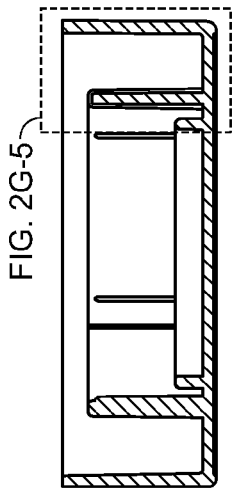
Figures 2, 2G, 3, 4, 5:
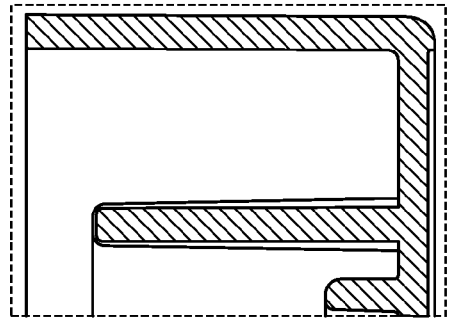
Figures 2, 2G:
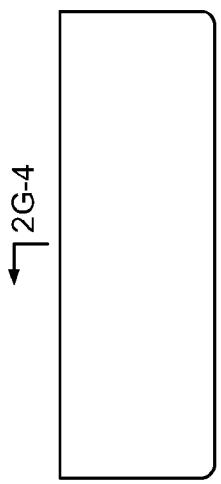
Figures 2, 2G, 3:
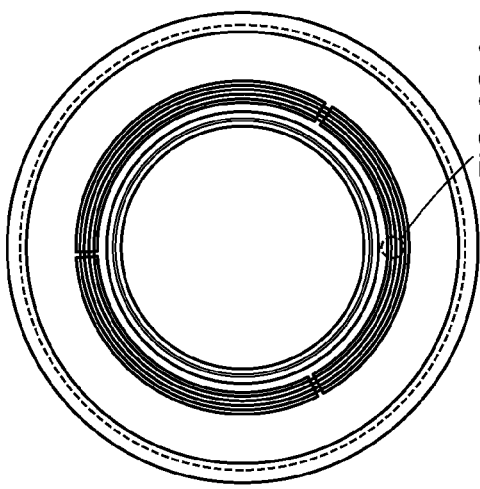
Figures 2, 2G, 3, 4, 5, 6:
Figures 1, 2G:
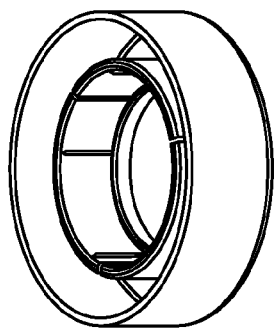

The invention features compositions and methods that are useful for any one of hydrating the skin, decreasing or preventing the occurrence of fine lines and/or wrinkles, decreases the level and or intensity of acne already present on the skin, decreasing the occurrence of future outbreaks of acne, and reducing skin inflammation.

The present invention relates to a composition comprising all natural substances, for topical administration, useful in the maintenance of skin hydration, the prevention and/or the treatment of the effects of skin aging, in particular fine lines and wrinkles, for the treatment and prevention of acne *vulgaris* (acne proprionis), and the limitation and reduction of skin inflammation. The claimed composition is an anhydrous mixture comprising probiotic bacteria, for topical administration to the skin.

In one embodiment of the invention, the composition of the invention is an anhydrous mixture of a probiotic bacteria and propylene glycol.

In certain embodiments, the mixture also comprises at least one of stearyl alcohol, sodium stearate, kaolin, *Streptococcus thermophilus*/Milk Ferment Lysate, glycerin, *Chamomilla recutita* (*Matricaria*) Flower Extract, myristyl alcohol, silica, astaxanthin, and inulin.

In certain embodiments the composition comprises an anhydrous mixture comprising at least one of a solvent, a skin penetrating agent, a thickening agent, a stabilizer, an emollient, a skin conditioner, a sugar, an abrasive and an absorbent.

In one embodiment, the mixture comprises propylene glycol at a concentration of about 30% to about 68%.

In another embodiment the composition comprises astaxanthin at a concentration of about 0.01% to about 1%.

In another embodiment, the composition comprises kaolin at a concentration of about 1% to about 10%.

In another embodiment, the concentration of the bacteria is about 1% to about 5%.

In another embodiment, the concentration of inulin is about 1% to about 5%.

In another embodiment, the concentration of stearyl alcohol is about 0.01% to about 20%.

In another embodiment, the concentration of sodium stearate is about 0.01-about 10%

In another embodiment, the concentration on glycerin is about 0.01% to about-10%

In another embodiment, the concentration of *Chamomilla recutita* flower extract is about 0.01% to about 3%

In another embodiment, the concentration of myrsistyl alcohol is about 0.01% to about 5%

In one embodiment, the composition comprises 65.96% propylene glycol, 2.64% glycerin, 11.37% stearyl alcohol, 1.11% myristyl alcohol, 7.07% sodium stearate, 1.33% chamomile extract, 1.11% silica, 3.88% kaolin, 2.77% inulin, 2.77% *Streptocossus thermophilus* 250 B and 0.01% astasanthin.

The invention also provides for an anhydrous mixture comprising a probiotic bacteria in combination with an over-the-counter treatment for acne, including but not limited to benzoyl peroxide, salicylic acid and sulfur. In one embodiment, benzoyl peroxide is at a concentration of about 2.5% to about 10%. In another embodiment, salicylic acid is present at a concentration of about 0.5% to about 2%. In another embodiment, sulfur is present at a concentration of about 3% to about 10%.

In one embodiment, the probiotic bacteria are freeze-dried.

In one embodiment, the mixture also comprises an over-the counter acne drug product, for example, benzoyl peroxide, salicylic acid and sulfur (see Guidance for Industry, Topical Acne Drug Products for Over-the Counter Human Use-Revision of Labeling and Classification of Benzoyl Peroxide as Safe and Effective, Small Entity Compliance Guide, U.S., Department of Health Sciences, Food and Drug Administration Center for Drug Evaluation and Research, June 2011).

In one embodiment, the mixture comprises benzoyl peroxide at a concentration of 2.5%.

The composition according to the invention is used for any one of hydrating the skin, reducing and/or preventing fine lines and wrinkles, treating acne and decreasing skin inflammation.

According to the methods of the invention, the composition is stable at room temperature. Preferably, the composition is packaged in a push-up tube. The invention provides for a method of any one of hydrating the skin, reducing and/or preventing fine lines and wrinkles, treating acne and decreasing skin inflammation, wherein the composition is applied in a thin layer to the entire effected area of the skin, for example, the face, back or chest. The composition is applied such that it covers the entire affected area, preferably once a day, or as needed. Once the composition is applied to the skin, the temperature and moisture of the skin activates the bacteria such that the bacteria become proliferative, fully function and colonize the skin. The composition is applied to the skin, preferably at night, on an as needed basis, or daily for maintenance of the skin.

Any compositions or methods provided herein can be combined with one or more of any of the other compositions and methods provided herein.

In one embodiment the composition is prepared as a solid.

In one embodiment the composition is packaged in a push-up tube or a pushscrew tube. Preferably, the composition of the invention is packaged in the push-up or screw-push tube in a solid form (see, for example, FIG. 1).

The following examples are put forth so as to provide those of ordinary skill in the art with a complete disclosure and description of how to make and use the vesicles and assay, screening, and therapeutic methods of the invention, and are not intended to limit the scope of what the inventors regard as their invention.

EXAMPLES

Example 1

Preparation of an Anhydrous Mixture of Probiotic Bacteria for Topical Application.

The anhydrous mixture of biologically active probiotic bacteria of the invention is prepared as follows.

Propylene Glycol is heated to 75° C. Preferably, propylene glycol is present at a concentration of about 30% to about 68%. Propylene Glycol is an aliphatic alcohol, and is a suitable base for the remaining components to be added into. Next, Astaxanthin AstaREAL® L10 is poured in, at a concentration of about 0.1% to about 1%. Astaxanthin is an organic compound and an antioxidant, which helps fight against the effects of oxygen. This is also what gives the product its distinctive color. In another embodiment, the mixture comprises an antioxidant selected from the group consisting of Ubiquinone CoQ10 and derivatives thereof which are free radical scavengers.

Under continuous propeller agitation, the Glycerin and Chamomile Extract are incorporated. *Chamomilla Recutita* (*Matricaria*) Flower Extract is the extract of the flower heads of the matricaria, *Chamomilla recutita*. Both ingredients are used for their skin conditioning properties and to achieve the desired texture of the final product. Next, the stearyl alcohol and myristyl alcohol are added in. Both are fatty alcohols that come in the form of waxes from the raw materials manufacturer. They are melted down and homogenized thoroughly prior to administration. Stearyl alcohol is a viscosity-increasing agent that works well with non-aqueous solutions. Myristyl alcohol stabilizes emulsions and acts as a conditioner.

With the propeller still mixing, the mixture is cooled. Once the tank temperature reaches 50° C., the following ingredients are added: Kaolin, about 1% to about 10%. Kaolin is a native hydrated aluminum silicate and is used as an abrasive and an absorbent. Silica is added in next. It is an inorganic oxide, which works well with the probiotic stick of the invention because of its suspending properties in non-surfactant formulations. Lastly, the *Streptococcus thermophilus*/Milk Ferment Lysate is added in at about 1% to about 5% in conjunction with the inulin at the same percentage range.

*Streptococcus thermophilus*/Milk Ferment Lysate is a lysate of the product obtained by the fermentation of milk by the microorganism, *Streptococcus thermophilus*.

*Streptococcus thermophilus* is a gram-positive facultative anaerobe. It is a cytochrome-, oxidase- and catalase-negative organism that is nonmotile, non-spore forming and homofermentative. *Streptococcus thermophilus* is an alpha-hemolytic species of the viridans group. It is also classified as a lactic acid bacteria (LAB). *Streptococcus thermophilus* is found in milk and milk products. It is a probiotic and used in the production of yogurt. *Streptococcus salivarus* subspecies *thermophilus* type 1131 is another probiotic strain. Additionally, *Bifidobacterium longum, Lactobacillus paracasei* and *Streptococcus salivarius*, can be added or substituted for the chosen bacteria.

The inulin is a purified cosmetic grade sugar that helps keep the beneficial bacteria viable.

This product is poured while hot and, preferably, immediately after mixing. If it is stored before pouring, it should be mixed again when it is heated up to pour.

In one embodiment, the method of the invention includes a step of freeze-drying the bacteria.

In another embodiment, the method of the invention includes a step of solidifying the mixture.

Example 2

An anhydrous mixture of probiotic bacteria for topical application is prepared as described in Example 1 above and comprises the following composition:

| Ingredient | Percentage |
| --- | --- |
| Propylene Glycol | 65.96 |
| Glycerin | 2.64 |
| Stearyl Alcohol | 11.37 |
| Myristyl Alcohol | 1.11 |
| Sodium Stearate | 7.07 |
| Chamomile Extract | 1.33 |
| Silica | 1.11 |
| Kaolin | 3.88 |
| Inulin | 2.77 |
| *Streptococcus Thermophilus* 250 B | 2.77 |
| Astaxanthin | 0.01 |

Example 3

A stick comprising an anhydrous mixture of probiotic bacteria is used for decreasing or treating acne.

In one embodiment, a subject is identified as in need of acne treatment, for example, by visual inspection by the subject and, optionally, by visual inspection by a healthcare professional.

Optionally, a sensitivity test is performed wherein the product is applied sparingly to at least one, for example one or two, affected areas during the first 3 days of use. If no discomfort follows, the stick is used as follows.

The anhydrous mixture of probiotic bacteria is applied topically, in a thin layer, to the entire affected area, for example the skin of the face, back or chest, preferably at night, at least once daily and/or, as needed. Preferably, the stick is rubbed directly onto a blemish.

A decrease in, or treatment of acne is determined by visual inspection following administration. A decrease can be seen as early as following a single administration, following administration daily for a week, following administration daily for a month or longer.

Preferably, this medication is not applied to individuals with sensitive skin. Preferably, when using the stick for treatment of acne, the individual being treated should avoid unnecessary sun exposure and use a sunscreen and avoid contact with eyes, lips and mouth. If skin irritation, characterized by redness, burning, itching, peeling or possibly swelling occurs, the product should be used less frequently or in a lower concentration.

Example 4

A stick comprising an anhydrous mixture of probiotic bacteria is used for decreasing/preventing fine lines and wrinkles.

In one embodiment, a subject is identified as in need of treatment, for example, by visual inspection by the subject and, optionally, by visual inspection by a healthcare professional.

Optionally, a sensitivity test is performed wherein the product is applied sparingly to at least one, for example one or two, affected areas or areas know to be susceptible to wrinkles, during the first 3 days of use. If no discomfort follows, the stick is used as follows.

The anhydrous mixture of probiotic bacteria is applied topically, in a thin layer to the entire affected area or to areas known to be susceptible to wrinkles, for example the face, preferably at night, at least once daily and/or, as needed.

A decrease in or prevention of wrinkles is determined by visual inspection following administration. A decrease can be seen earlier as following a single administration, following administration daily for a week, following administration daily for a month or longer.

Preferably, this medication is not applied to individuals with sensitive skin. Preferably, when using the stick for treatment or prevention of wrinkles, the individual being treated should avoid unnecessary sun exposure and use a sunscreen and avoid contact with eyes, lips and mouth. If skin irritation, characterized by redness, burning, itching, peeling or possibly swelling occurs, the product should be used less frequently or in a lower concentration.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

We claim:

1. An anhydrous topical probiotic composition comprising a probiotic bacteria, wherein the probiotic bacteria are freeze-dried and in a viable, nonproliferative state;
   inulin; and
   a thickening agent,
   wherein the bacteria, the inulin, and the thickening agent are formulated into a solid for topical administration to the skin.

2. The composition of claim 1, wherein the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius*.

3. The composition of claim 1, further comprising at least one of: propylene glycol, glycerin, sodium stearate, kaolin, *Chamomilla recutita* flower extract, myristyl alcohol, silica steary alcohol, and astaxanthin.

4. The composition of claim 3, wherein the concentration of propylene glycol is about 30% to about 68%.

5. The composition of claim 3, wherein the concentration of astaxanthin is about 0.01% to about 1%.

6. The composition of claim 3, wherein the concentration of kaolin is about 1% to about 10%.

7. The composition of claim 3, wherein the thickening agent is stearyl alcohol in a concentration of about 0.01% to about 20%.

8. The composition of claim 3, wherein the concentration of sodium stearate is about 0.01 to about 10%.

9. The composition of claim 3, wherein the concentration on glycerin is about 0.01% to about 10%.

10. The composition of claim 3, wherein the concentration of *Chamomilla recutita* flower extract is about 0.01% to about 3%.

11. The composition of claim 3, wherein the concentration of myrsistyl alcohol is about 0.01% to about 5%.

12. The composition of claim 3, wherein the concentration of silica is about 1% to about 10%.

13. The composition of claim 3, where in the composition comprises 65.96% propylene glycol, 2.64% glycerin, 11.37% stearyl alcohol, 1.11% myristyl alcohol, 7.07% sodium stearate, 1.33% *Chamomilla recutita* flower extract, 1.11% silica, 3.88% kaolin, 2.77% inulin and 0.01% astaxanthin, and wherein the probiotic is *Streptococcus thermophiles* 250 B at a concentration of 2.77%.

14. The composition of claim 1, wherein the concentration of inulin is about 1% to about 5%.

15. The composition of claim 1, wherein the composition is packaged in a push-up tube.

16. The composition of claim 1, further comprising at least one of benzoyl peroxide, salicylic acid and sulfur.

17. The composition of claim 16, wherein the concentration of benzoyl peroxide is 2.5%.

18. The composition of claim 1, wherein the composition hydrates the skin, decreases or prevents fine lines and wrinkles, limits and reduces skin inflammation, prevents future outbreaks of acne, or decreases acne that is already present on the skin.

19. A stick comprising the composition of claim 1.

20. An anhydrous composition for topical administration to the skin comprising a probiotic bacteria wherein the probiotic bacteria are freeze-dried and in a viable, nonproliferative state, propylene glycol, stearyl alcohol, sodium stearate, kaolin, *Streptococcous Thermophilus*, glycerin, *Chamomilla Recutita* flower extract, myristyl alcohol, asthaxantin, inulin, silica and benzoyl peroxide at a concentration of about 2.5% to about 10%.

21. A solid anhydrous composition for topical administration to the skin comprising wherein the probiotic bacteria are freeze-dried and in a viable, nonproliferative state;
  wherein the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius*;
  further comprising at least one of: propylene glycol, glycerin, stearyl alcohol, sodium stearate, kaolin, *Chamomilla recutita* flower extract, myristyl alcohol, silica, astaxanthin and inulin;
  wherein the concentration of propylene glycol is about 30% to about 68%; or
  wherein the concentration of astaxanthin is about 0.01% to about 1%; or
  wherein the concentration of kaolin is preferably about 1% to about 10%; or
  wherein the concentration of the bacteria is preferably about 1% to about 5%; or
  wherein the concentration of inulin is about 1% to about 5%; or
  wherein the concentration of stearyl alcohol is about 0.01% to about 20%; or
  wherein the concentration of sodium stearate is about 0.01 to about 10%; or
  wherein the concentration on glycerin is about 0.01% to about 10%; or
  wherein the concentration of *Chamomilla recutita* flower extract is about 0.01% to about 3%; or
  wherein the concentration of myrsistyl alcohol is about 0.01% to about 5%; or
  wherein the concentration of silica is about 1% to about 10%.

22. The composition of claim 21, further comprising at least one of benzoyl in an amount of 2.5% to about 10%, salicylic acid and sulfur.

23. A solid anhydrous composition in the form of a stick for topical administration to the skin comprising wherein the probiotic bacteria are freeze-dried and in a viable, nonproliferative state;
  wherein the bacteria is selected from the group consisting of: *Streptococcus thermophilus, Streptococcus salivarus* subspecies *thermophilus* type 1131, *Bifidobacterium longum, Lactobacillus paracasei* and *Streptococcus salivarius*;
  further comprising at least one of: propylene glycol, glycerin, stearyl alcohol, sodium stearate, kaolin, *Chamomilla recutita* flower extract, myristyl alcohol, silica, astaxanthin and inulin;
  wherein the concentration of propylene glycol is about 30% to about 68%; or
  wherein the concentration of astaxanthin is about 0.01% to about 1%; or
  wherein the concentration of kaolin is preferably about 1% to about 10%; or
  wherein the concentration of the bacteria is preferably about 1% to about 5%; or
  wherein the concentration of inulin is about 1% to about 5%; or
  wherein the concentration of stearyl alcohol is about 0.01% to about 20%; or
  wherein the concentration of sodium stearate is about 0.01 to about 10%; or
  wherein the concentration on glycerin is about 0.01% to about 10%; or
  wherein the concentration of *Chamomilla recutita* flower extract is about 0.01% to about 3%; or
  wherein the concentration of myrsistyl alcohol is about 0.01% to about 5%; or
  wherein the concentration of silica is about 1% to about 10%.

24. The composition of claim 23, further comprising at least one of benzoyl in an amount of 2.5% to about 10%, salicylic acid and sulfur.

25. A method of colonizing with probiotic bacteria the skin of an individual in need thereof, comprising topically administering to the skin of the individual the composition of claim 1 to the skin.

26. A method of decreasing acne/treating acne of the skin of an individual in need thereof, comprising topically administering to the skin of the individual the composition of claim 1.

27. A method of decreasing or preventing fine lines and wrinkles of the skin of an individual in need thereof, comprising topically administering to the skin of the individual the composition of claim 1.

28. A method of maintaining the hydration of the skin of an individual in need thereof, comprising topically administering to the skin of the individual the composition of claim 1.

29. A method of reducing skin inflammation of the skin of an individual in need thereof, comprising topically administering to the skin of the individual the composition of claim 1.

* * * * *